United States Patent [19]

Choe et al.

[11] Patent Number: 4,707,305

[45] Date of Patent: Nov. 17, 1987

[54] NAPHTHOQUINODIMETHANE COMPOSITIONS

[75] Inventors: Eui W. Choe, Randolph; Alan Buckley, Berkeley Heights, both of N.J.; Anthony F. Garito, Radnor, Pa.

[73] Assignee: Celanese Corporation, New York, N.Y.

[21] Appl. No.: 864,203

[22] Filed: May 19, 1986

Related U.S. Application Data

[63] Continuation-in-part of Ser. No. 748,583, Jun. 25, 1985, Pat. No. 4,640,800.

[51] Int. Cl.$^4$ .............................................. C07C 50/14
[52] U.S. Cl. ................................. 260/396 N; 544/88; 544/111; 544/242; 544/359; 546/191; 548/217; 548/300; 558/428
[58] Field of Search ................... 260/396 N; 558/430; 548/300, 217; 544/88

[56] References Cited

U.S. PATENT DOCUMENTS

| | | | |
|---|---|---|---|
| 3,526,497 | 9/1970 | Obreiter | 260/396 N X |
| 4,478,751 | 10/1984 | Jonas et al. | 260/396 N |
| 4,568,494 | 2/1986 | Jonas et al. | 260/396 N |

Primary Examiner—Joseph Paul Brust
Attorney, Agent, or Firm—Depaoli & O'Brien

[57] ABSTRACT

This invention provides a novel class of naphthoquinodimethane compositions. Illustrative of the invention is 11,11-di(n-hexyldecylamino)-12,12-dicyano-2,6-naphthoquinodimethane:

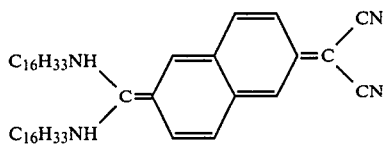

An invention naphthoquinodimethane compound has utility as a nonlinear optical component in an electrooptic light modulator device.

11 Claims, No Drawings

NAPHTHOQUINODIMETHANE COMPOSITIONS

This patent application is a continuation-in-part of patent application Ser. No. 748,583, filed Jun. 25, 1985, now U.S. Pat. No. 4,640,800.

BACKGROUND OF THE INVENTION

It is known that organic and polymeric materials with large delocalized $\pi$-electron systems can exhibit nonlinear optical response, which in many cases is a much larger response than by inorganic substrates.

In addition, the properties of organic and polymeric materials can be varied to optimize other desirable properties, such as mechanical and thermoxidative stability and high laser damage threshold, with preservation of the electronic interactions responsible for nonlinear optical effects.

Thin films of organic or polymeric materials with large second-order nonlinearities in combination with silicon-based electronic circuitry have potential as systems for laser modulation and deflection, information control in optical circuitry, and the like.

Other novel processes occurring through third-order nonlinearity such as degenerative four-wave mixing, whereby real-time processing of optical fields occurs, have potential utility in such diverse fields as optical communications and integrated circuit fabrication.

Of particular importance for conjugated organic systems is the fact that the origin of the nonlinear effects is the polarization of the $\pi$-electron cloud as opposed to displacement or rearrangement of nuclear coordinates found in inorganic materials.

Nonlinear optical properties of organic and polymerlic materials was the subject of a symposium sponsored by the ACS division of Polymer Chemistry at the 18th meeting of the American Chemical Society, Sep. 1982. Papers presented at the meeting are published in ACS Symposium Serial 233, American Chemical Society, Washington, D.C. 1983.

The above-recited publications are incorporated herein by reference.

Of more specific interest with respect to the present invention embodiments is prior art relating to tetracyanoquinodimethane compounds, such as U.S. Pat. Nos. 3,115,506; 3,226,389; 3,408,367; 3,681,353; 3,687,987; 3,953,874; 4,229,364; and 4,478,751.

There is continuing research effort to develop new nonlinear optical organic systems for prospective novel phenomena and devices adapted for laser frequency conversion, information control in optical circuitry, light valves and optical switches. The potential utility of organic materials with large second-order and third-order nonlinearities for very high frequency application contrasts with the bandwidth limitations of conventional inorganic electrooptic materials.

Accordingly, it is an object of this invention to provide organic compositions which are characterized by a large delocalized conjugated $\pi$-electron system which can exhibit nonlinear optical response.

It is another object of this invention to provide a novel class of organic compounds which is characterized by a charge asymmetric quinodimethane conjugated structure.

It is a further object of this invention to provide high performance nonlinear optical substrates.

Other objects and advantages of the present invention shall become apparent from the accompanying description and examples.

DESCRIPTION OF THE INVENTION

One or more objects of the present invention are accomplished by the provision of a novel class of charge asymmetric conjugated naphthoquinodimethane compositions.

The term "charge asymmetric" as employed herein refers to the dipolarity characteristic of organic molecules containing an electron-withdrawing group which is in conjugation with an electron-donating group.

Illustrative of the invention class of compositions are quinodimethane compounds corresponding to the structural

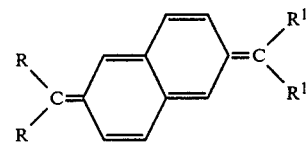

where R and $R^1$ are substituents selected from hydrogen and aliphatic, alicyclic and aromatic groups containing between about 1–20 carbon atoms, and at least one of the R substituents is an electron-donating group, and at least one of the $R^1$ substituents is an electron-withdrawing group.

Illustrative of $R^1$ electron-withdrawing substituents are cyano, nitro, trifluoromethyl, tricyanoethylene, and the like. $R^1$ alternatively can be hydrogen or an aliphatic, cycloaliphatic or aromatic group such as methyl, chloroethyl, methoxyethyl, pentyl, decyl, 2-propenyl, 2-propynyl, cyclohexyl, phenyl, tolyl, and the like.

The $=CR^1R^1]$ moiety can also represent a cyclic structure which is electron-withdrawing, such as:

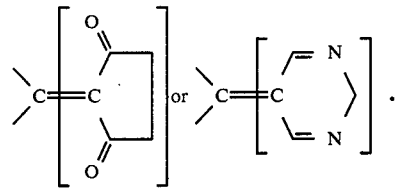

Illustrative of R electron-donating substituents are amino, alkylamino, alkenylamino, alkynylamino, alkoxy, thioalkyl, phosphinyl, and the like. R alternatively can be hydrogen or an aliphatic, cycloaliphatic or aromatic group as described for the $R^1$ substituent above The [RRC= moiety can also represent a cyclic structure which is electron-donating, such as:

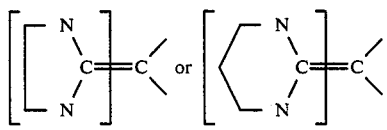

Illustrative of preferred naphthoquinodimethane compounds are those in which the pair of R substituents are the same electron-donating groups, and the pair of $R^1$ substituents are the same electron-withdrawing groups.

An important aspect of the present invention is the provision of a naphthoquinodimethane type compound which has utility as a charge asymmetric component of nonlinear optical media.

Naphthoquinodimethane structures of preference are those corresponding to the formula:

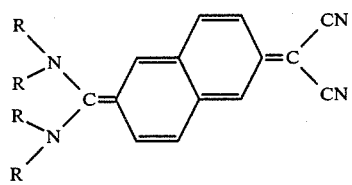

where R is hydrogen or an alkyl group. Illustrative of alkyl groups are methyl, ethyl, propyl, isopropyl, butyl, isobutyl, pentyl, decyl, hexadecyl, eicosyl, and the like. Alkyl groups containing between about 1-20 carbon atoms are preferred. The $NR_2$ group can also represent a heterocyclic structure such as piperidyl, piperazyl or morpholinyl.

The $=C(NR_2)_2$ moiety in the formulae can constitute a heterocyclic radical in which the two amino groups taken together with the connecting methylidene carbon atom form a cyclic structure such as imidazoline in the naphthoquinodimethane compound:

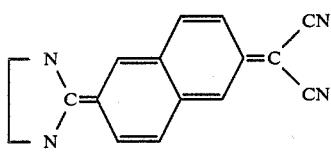

The naphthoquinodimethane compounds can also contain substituents which have one or more optically active asymmetric centers, such as chiral isomeric structues corresponding to the formula:

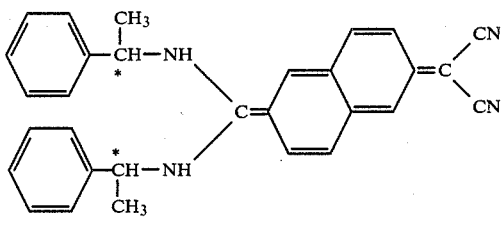

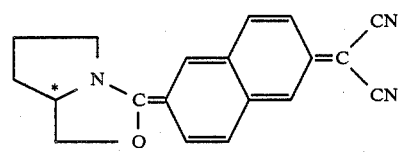

In all of the naphthoquinodimethane structural formulae illustrated herein the cyclic groups can have one or more of the hydrogen positions on the ring carbon atoms replaced with a substituent such as alkyl, halo, alkoxy, phenyl, and the like, or can be integrated as part of a more complex fused polycyclic ring structure.

A compound such as 11,11-diamino-12,12-dicyanonaphtho-2,6-quinodimethane can be synthesized from 2,6-dimethylnaphthalene in accordance with the following series of chemical rection steps:

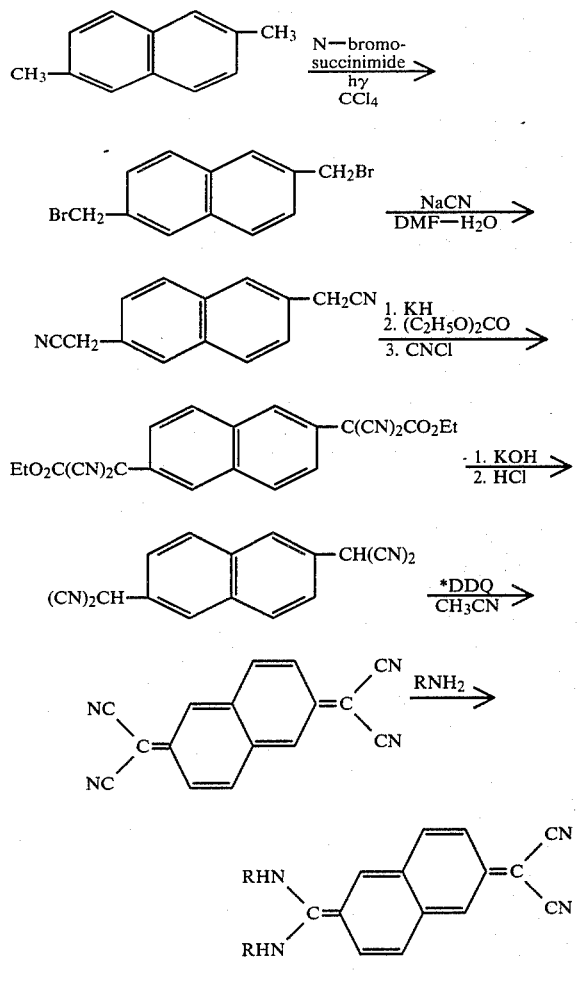

*2,3-dichloro-5,6-dicyanobenzoquinone

R is H or alkyl (e.g., $C_{16}H_{33}$)

The synthesis of 11,11,12,12-tetracyanonaphtho-2,6-quinodimethane from 2,6-dimethylnaphthalene or 2,6-bis(bromomethyl)naphthalene is described in J. Org. Chem., 28, 2719(1963) and J. Org. Chem., 39 (No. 8), 1165(1974).

Nonlinear Optical Properties

A quinodimethane compound of the present invention can be utilized as a charge asymmetric component of a nonlinear optical medium.

Thus, in another embodiment this invention can provide a nonlinear optical organic medium exhibiting a $\chi^{(2)}$ susceptibility of at least about $1\times10^{-6}$ esu, and wherein the substrate comprises a noncentrosymmetric configuration of molecules having a naphthoquinodimethane structure corresponding to the formula:

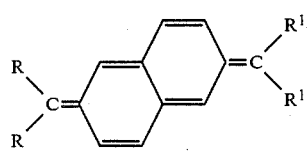

where R and $R^1$ are substituents selected from hydrogen and aliphatic, alicyclic and aromatic groups containing between about 1–20 carbon atoms, and at least one of the R substituents is an electron-donating group, and at least one of the $R^1$ substituents is an electron-withdrawing group. R and $R^1$ are substituents as previously defined and illustrated.

In another embodiment this invention can provide a nonlinear optical organic medium exhibiting a $\chi^{(2)}$ susceptibility of at least about $1 \times 10^{-6}$ esu, an absence of interfering fluorescence in the wavelength range between about 0.3–3 μm, an optical loss less than about 0.1 decibel per kilometer, a response time less than about $10^{-13}$ second, phase matching of fundamental and second harmonic frequencies, a dielectric constant less than about 5, and wherein the medium comprises a noncentrosymmetric configuration of molecules having a quinodimethane conjugated structure corresponding to the formula:

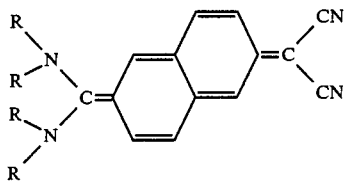

where R is a substituent selected from hydrogen and alkyl groups

The naphthoquinodimethane molecules can have an external field-induced uniaxial molecular orientation in a host liquid medium, or an external field induced stable uniaxial molecular orientation in a host solid medium. A substrate of unaligned quinodimethane molecules exhibits third order nonlinear optical response.

In another embodiment this invention can provide an optically transparent medium comprising a noncentrosymmetric or centrosymmetric configuration of an 11,11-diamino-12,12-dicyanonaphtho-2,6-quinodimethane type or an 11,11-di(alkylamino)-12,12-dicyanonaphtho-2,6-quinodimethane type of molecules.

In a further embodiment this invention can provide a nonlinear optical medium comprising a solid polymeric matrix having incorporated therein a distribution of 11,11-diamino-12,12-dicyanonaphtho-2,6-quinodimethane or 11,11-di(alkylamino)-12,12-dicyanonaphtho-2,6-quinodimethane molecules.

The term "Miller's delta" as employed herein with respect to second harmonic generation (SHG) is defined by Garito et al in Chapter 1, "Molecular Optics:-Nonlinear Optical Properties Of Organic And Polymeric Crystals"; ACS Symposium Series 233 (1983).

The quantity "delta"(δ) is defined by the equation:

$$D_{ijk} = \epsilon_o \chi_{ii}^{(1)} \chi_{jj}^{(1)} \chi_{kk}^{(1)} \delta_{ijk}$$

where terms such as $\chi_{ii}^{(1)}$ are the linear susceptibility components, and $d_{ijk}$, the second harmonic coefficient, is defined through $$\chi_{ijk}^{(2)}(-2\omega; \omega, \omega) = 2 d_{ijk}(-2\omega; \omega, \omega)$$

The Miller's delta ($10^{-2}$ m$^2$/c at 1.06 μ) of various nonlinear optical crystalline substrates are illustrated by KDP (3.5), LiNbO$_3$ (7.5), GaAs (1.8) and 2-methyl-4-nitroaniline (160).

Such comparative figures of merit are defined over the. frequency range extending to zero frequency, or equivalently DC, and the polarization electrooptic coefficient as described in the publication by Garito et al recited above.

The term "fluorescence" as employed herein refers to an optical effect in which a molecule is excited by short wavelength light and emits light radiation at a longer wavelength. The fluorescence effect is described with respect to liquid dye lasers in Optoelectronics, An Introduction, pages 233–236, Prentice Hall International, Englewood Cliffs, N.J. (1983).

The term "optical loss" as employed herein is defined by the equation:

$$\alpha L = 10 \log (I_o/I)$$

where
α = attenuation coefficient ratio of lost light per unit length
L = sample length
$I_o$ = intensity of incident light
I = intensity of transmitted light.

The term "optical scattering loss" is defined and measured quantitatively by $$T_{195}/T_{\parallel}$$

where $T_\perp$ is the transmission of optical radiation through the test sample between polarizers perpendicular to each other, and $T_{\parallel}$ is the transmission between polarizers parallel to each other.

The term "response time" as employed herein refers to numerous physical mechanisms for nonlinear optical responses and properties of nonlinear optical materials. The fastest intrinsic response time to light radiation is a physical mechanism based on electronic excitations characterized by a response time of about $10^{-14}$–$10^{-15}$ seconds. Response time is a term descriptive of the time associated with optical radiation causing promotion of an electron from the electronic ground state to an electronic excited state and subsequent de-excitation to the electronic ground state upon removal of the optical radiation.

The term "phase matching" as employed herein refers to an effect in a nonlinear optical medium in which a harmonic wave is propagated with the same effective refractive index as the incident fundamental light wave. Efficient second harmonic generation requires a nonlinear optical medium to possess propagation directions in which optical medium birefringence cancels the natural dispersion, i.e., the optical transmission of fundamental and second harmonic frequencies is phase matched in the medium. The phase matching can provide a high conversion percentage of the incident light to the second harmonic wave.

For the general case of parametric wave mixing, the phase matching condition is expressed by the relationship:

$$n_1\omega_1 + n_2\omega_2 = n_3\omega_3$$

where $n_1$ and $n_2$ are the indexes of refraction for the incident fundamental radiation, $n_3$ is the index of refraction for the created radiation, $\omega_1$ and $\omega_2$ are the frequencies of
the incident fundamental radiation and $\omega_3$ is the frequency of the created radiation. More particularly, for second harmonic generation, wherein $\omega_1$ and $\omega_2$ are the same frequency $\omega$, and $\omega_3$ is the created second harmonic frequency $2\omega$, the phase matching condition is expressed by the relationship:

$$n_\omega = n_{2\omega}$$

where $n_\omega$ and $n_{2\omega}$ are indexes of refraction for the incident fundamental and created second harmonic light waves, respectively. More detailed theoretical aspects are described in "Quantum Electronics" by A. Yariv, chapters 16–17 (Wiley and Sons, New York, 1975).

The term "dielectric constant" as employed herein is defined in terms of capacitance by the equation:

$$\epsilon = C/C_o$$

where
C = capacitance when filled with a material of dielectric constant
$C_o$ = capacitance of the same electrical condenser filled with air The term "external field" as employed herein refers to an electric or magnetic field or mechanical stress which is applied to a medium of mobile organic molecules, to induce dipolar alignment of the molecules parallel to the field or stress direction.

The term "optically transparent" as employed herein refers to an optical medium which is transparent or light transmitting with respect to incident fundamental light frequencies and created light frequencies. In a nonlinear optical device, a present invention nonlinear optical medium is transparent to both the incident and exit light frequencies.

The fundamental concepts of nonlinear optics and their relationship to chemical structures can be expressed in terms of dipolar approximation with respect to the polarization induced in an atom or molecule by an external field, as summarized in the ACS Symposium Series 233 (1983).

Field-induced Microscopic Nonlinearity

The microscopic response, or electronic susceptibility $\beta$, and its frequency dependence or dispersion, is experimentally determined by electric field induced second harmonic generation (DCSHG) measurements of liquid solutions or gases as described in "Dispersion Of The Nonlinear Second Order Optical Susceptibility Of Organic Systems", Physical Review B, 28 (No. 12), 6766 (1983) by Garito et al, and the Molecular Crystals and Liquid Crystals publication cited above.

In the measurements, the created frequency $\omega_3$ is the second harmonic frequency designated by $2\omega$, and the fundamental frequencies $\omega_1$ and $\omega_2$ are the same frequency designated by $\omega$. An applied DC field removes the natural center of inversion symmetry of the solution, and the second harmonic signal is measured using the wedge Maker fringe method. The measured polarization at the second harmonic frequency $2\omega$ yields the effective second harmonic susceptibility of the liquid solution and thus the microscopic susceptibility $\beta$ for the molecule.

The present invention class of novel organic compounds exhibits extremely large values of $\beta$ because of a noncentrosymmetric naphthoquinodimethane structure. Illustrative of this class of compounds are 11,11-di(hexydecylamino)-12,12-dicyano-2,6-naphtho quino-dimethane and 11,11-di(dimethylamino)-12,12-dicyano-2,6-naphthoquinodimethane:

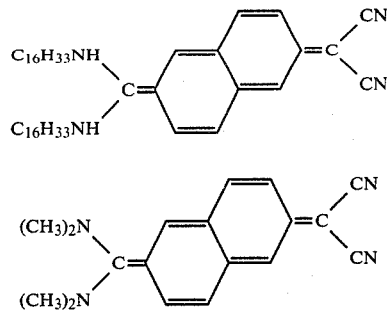

The theory and practice of high performance nonlinear optical media, with specific reference to quinodimethane compounds, is elaborated in copending patent application Ser. No. 748,617, filed Jun. 25, 1985; incorporated herein by reference.

Langmuir-Blodgett Deposition Technique

The Langmuir-Blodgett technique is reviewed in J. Macromol. Sci.-Rev. Macromol. Chem., C21(1), 61(1981); incorporated herein by reference.

An extensive elaboration of Langmuir-Blodgett technology is published in Thin Solid Films, Vol. 99(1983), which includes papers presented at the First International Conference On Langmuir-Blodgett Films, Durham, Great Britain, Sep. 20–22, 1982; Elsevier Sequoia S.A., Lausanne; incorporated herein by reference.

In 1917 Irving Langmuir developed the experimental and theoretical concepts which underlie our understanding of the behavior of organic molecules in insoluble monolayers on the surface of water. Langmuir demonstrated that long-chain fatty acids on the surface of water form films in which the molecules occupy the same cross-sectional area whatever the chain length of the molecules. The films are one molecule thick, and the molecules are oriented at the water surface, with the polar functional group immersed in the water and the long nonpolar chain directed nearly vertically up from the water surface.

This understanding of the nature of insoluble monolayers was facilitated by the development of a surface balance, which is associated with Langmuir's name.

In 1919 Langmuir reported a development in which fatty acid monolayers on water surfaces were transferred to solid supports such as glass slides. In 1933 Katherine Blodgett announced the discovery that sequential monolayer transfer could be accomplished to form built-up multilayer films, i.e., unitary laminate structures now universally referred to as "Langmuir-Blodgett films".

Grunfeld et al in Thin Solid Films, 99, 249 (1983) demonstrate the application of a Langmuir-Blodgett layer as a potentially useful integrated optics component by employing the optical absorption anisotropy of a diacetylene film in a polarization mode filter.

The present invention naphthoquinodimethane compositions are amenable to Langmuir-Blodgett deposition procedures for the formation of monolayer and multilayer continuous film coatings on solid substrates such as optical glass. The coated substrates exhibit nonlinear optical properties.

The following examples are further illustrative of the present invention. The components and specific ingredients are presented as being typical, and various modifications can be derived in view of the foregoing disclosure within the scope of the invention.

Fluorescence activity in a nonlinear optical substrate is measured by Perkin-Elmer Fluorescence Spectroscopy Model No. MPF-66 or LS-5.

Optical loss exhibited by a nonlinear optical substrate is measured by optical time domain reflectometry or optical frequency-domain reflectometry as described in "Single-mode Fiber Optics" by Luc B. Jeunhomme, Marcel Dekker Inc., N.Y., 1984. It is also measured by the method described in "The Optical Industry And Systems Purchasing Directory", Photonics, 1984. The scattering optical loss is quantitatively measured by the ratio of perpendicular transmission to parallel transmission of a He-Ne laser beam through the nonlinear sample which is placed between crossed polarizers.

The response time of a nonlinear optical substrate is calculated by the method described in "Optoelectronics; An Introduction" by P. J. Deau, Editor, Prentice-Hall International.

The dielectric constant of a nonlinear optical substrate is measured by the methods described in Chapter XXXVIII of "Technique of Organic Chemistry", Volume I, Part III, (Physical Methods of Organic Chemistry) by Arnold Weissberger, Editor, Interscience Publishers Ltd., New York, 1960.

EXAMPLE I

This Example illustrates the preparation of 11,11-diamino-12,12-dicyano-2,6-naphthoquinodimethane in accordance with the present invention.

Ten grams of 11,11,12,12-tetracyano-2,6-naphthoquinodimethane prepared by a synthetic scheme as previously described [J. Org. Chem., 39 (No. 8), 1165 (1974)] and 2 liters of tetrahydrofuran are placed in a three-necked three-liter flask equipped with a mechanical stirrer, a nitrogen inlet, a drying tube and a gas-inlet connected to an anhydrous ammonia gas tank. Ammonia gas is bubbled through the stirred solution for three days at room temperature. The crude product in precipitate form is filtered from the reaction mixture, washed with distilled water, and recrystallized from N,N-dimethylformamide (DMF)-water to yield high purity 11,11-diamino-12,12-dicyano-2,6-naphthoquinodimethane product. DC induced second harmonic generation can achieve a second order nonlinear optical susceptibility $\beta$ of about $300 \times 10^{-30}$ esu, an optical susceptibility $\chi^{(2)}$ of about $10 \times 10^{-6}$ esu, and a Miller's delta of about 4 square meters/coulomb.

When the NLO substrate is centrosymmetric in macroscopic configuration, it can exhibit a nonlinear optical susceptibility $\chi^{(3)}$ of about $1 \times 10^{-10}$ esu, a response time of less than $10^{-13}$ second, an absence of fluorescence in the wavelength range between about 0.3–3 $\mu$m, an optical loss less than about 0.1 decibel per kilometer, and a dielectric constant less than about 5.

EXAMPLE II

This Example illustrates the preparation of 11,11-di(n-butylamino)-12,12-dicyano-2,6-naphthoquinodimethane in accordance with the present invention.

A three-necked three-liter flask equipped with a mechanical stirrer, a nitrogen inlet, a drying tube, and an addition funnel is charged with 10 grams (0.03 moles) of 11,11,12,12-tetracyano-2,6-naphthoquinodimethane and two liters of tetrahydrofuran. Twenty-nine grams (0.12 moles) of n-butylamine in 100 ml of tetrahydrofuran is added dropwise into the flask, and the resulting mixture is stirred for three days at room temperature. The resulting THF solution is concentrated on a rotary evaporator.

The crude product in precipitate form is separated by filtration, washed with distilled water, neutralized with 10% solution of ammonium hydroxide, washed with water, and then recrystallized from DMF-water to yield 11,11-di(n-butylamino)-12,12-dicyanonaphthoquinodimethane.

This compound is aligned in a melt-phase in a DC field by applying about 15 Kvolts/cm, and cooled slowly to freeze the aligned molecular structure in the DC field. The aligned molecular structure is optically transparent and can exhibit a nonlinear optical susceptibility $\beta$ of about $350 \times 10^{-30}$ esu, a $\chi^{(2)}$ of about $1.5 \times 10^{-6}$ esu, and a Miller's delta of about 4 square meters/coulomb.

In a transparent solid medium in which the molecules are randomly distributed, the product can exhibit a nonlinear optical susceptibility $\chi^{(3)}$ of about $1 \times 10^{-10}$ esu. The other properties are similar to those described for the Example I product.

EXAMPLE III

This Example illustrates the preparation of 11,11-di(n-hexyldecylamino)-12,12-dicyano-2,6-naphthoquinodimethane.

Following the procedure of Example II, 11,11-di(n-hexadecylamino)-12,12-dicyano-2,6-naphthoquinodimethane is prepared by employing a tetrahydrofuran solution containing ten grams of 11,11,12,12-tetracyano-2,6-naphthoquinodimethane and thirty-two grams of n-butylamine. The second order nonlinear susceptibility $\beta$ is about $200 \times 10^{-30}$ esu after alignment of molecules in a DC field, or after alignment of molecules by the Langmuir-Blodgett Technique in which a monolayer or several layers of molecules are deposited on a glass substrate.

EXAMPLE IV

This Example illustrates the use of 11,11-di(n-hexyldecylamino)-12,12-dicyano-2,6-naphtho quinodimethane as a guest molecule in a polymer substrate.

Ten grams of 11,11-di(n-hexadecylamino)-12,12-dicyano-2,6-naphthoquinodimethane and 90 grams of poly(methyl methacrylate) are dissolved in 400 ml of methylene chloride. A film (2 mil) is cast from this solution on a glass plate coated with indium tin oxide. Another glass plate coated with indium tin oxide is placed on the film, and then the film is heated to about 150° C. A DC field is applied to align the molecules, and the film is cooled slowly in the applied field to yield an aligned polymer alloy which can have a second order nonlinear susceptibility $\beta$ of about $300 \times 10^{-30}$ esu.

What is claimed is:

1. A naphthoquinodimethane composition corresponding to the formula:

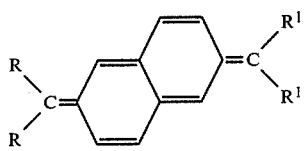

where R and R¹ are substituents selected from hydrogen and aliphatic, alicyclic and aromatic groups containing between about 1–20 carbon atoms, and at least one of the R substituents is an electron-donating group, or the group

is

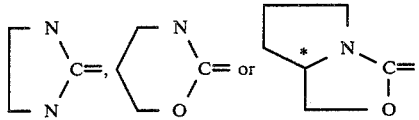

and at least one of the R¹ substituents is a cyano group.

2. A naphthoquinodimethane composition in accordance with claim 1 wherein at least one R substituent is an amino group.

3. A naphthoquinodimethane composition in accordance with claim 1 wherein the other R¹ is a nitro group.

4. A naphthoquinodimethane composition in accordance with claim 1 wherein the other R¹ is a trifluoromethyl group.

5. A naphthoquinodimethane composition in accordance with claim 1 wherein each R substituent is an amino group.

6. A naphthoquinodimethane composition in accordance with claim 1 wherein each R¹ is a cyano group.

7. A naphthoquinodimethane composition in accordance with claim 1 wherein at least one R¹ substituent is a chiral group.

8. A naphthoquinodimethane composition corresponding to the formula:

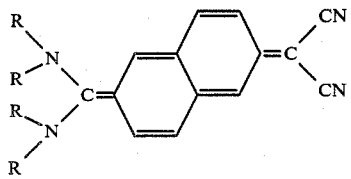

where R is a substituent selected from hydrogen and alkyl groups containing between about 1–20 carbon atoms.

9. 11,11-diamino-12,12-dicyano-2,6-naphthoquinodimethane.

10. 11,11-di(n-butylamino)-12,12-dicyano-2,6-naphthoquinodimethane.

11. 11,11-ki(n-hexadecylamino)-12,12-dicyano-2,6-naphthoquinodimethane.

* * * * *